United States Patent [19]

Steffen

[11] Patent Number: 5,849,949
[45] Date of Patent: Dec. 15, 1998

[54] PROCESS FOR PREPARING ALKYL- AND ARYLMALONIC ACIDS

[75] Inventor: Klaus-Dieter Steffen, Hennef, Germany

[73] Assignee: Huels Aktiengesellschaft, Marl, Germany

[21] Appl. No.: 64,005

[22] Filed: Apr. 21, 1998

[30] Foreign Application Priority Data

Apr. 21, 1997 [DE] Germany .................. 197 16 615.6

[51] Int. Cl.[6] .................................................. C07C 51/00
[52] U.S. Cl. ......................... 562/483; 562/506; 562/590
[58] Field of Search ................................... 562/506, 590, 562/483

[56] References Cited

PUBLICATIONS

Derwent=WPIDS; 79–42946b; abstract of jp54052054, Apr. 1979.

*Primary Examiner*—Samuel Barts
*Attorney, Agent, or Firm*—Oblon, Spivak, McClelland, Maier & Neustadt, P.C.

[57] ABSTRACT

Alkyl- and arylmalonic acids of the formula I

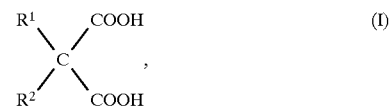

where $R^1$=H, $C_1$–$C_{12}$-alkyl, phenyl, $C_1$–$C_4$-alkylphenyl, $C_2$–$C_4$-dialkylphenyl, $R^2$=$C_1$–$C_{12}$-alkyl, phenyl, $C_1$–$C_4$-alkylphenyl, $C_2$–$C_4$-dialkylphenyl or $R^1$+$R^2$=—$CH_2$—$CH_2$—, are prepared by alkaline saponification by hydrolyzing the corresponding $C_1$–$C_4$-alkyl esters of the malonic acid of formula I, with alkali metal hydroxide dissolved in an aqueous alkali metal salt solution containing salt at 90–100% of saturation, acidifying the hydrolysis product with a mineral acid, removing the precipitated alkali metal salt which forms upon acidification, and extracting the alkyl- and arylmalonic acid formed from the aqueous solution with the aid of an organic solvent.

11 Claims, No Drawings

PROCESS FOR PREPARING ALKYL- AND ARYLMALONIC ACIDS

BACKGROUND OF THE INVENTION

Field of the Invention

The present invention relates to a process for preparing alkyl- and arylmalonic acids of the formula I

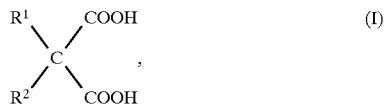

where
$R^1$=H, $C_1$–$C_{12}$-alkyl, phenyl, $C_1$–$C_4$-alkylphenyl, $C_2$–$C_4$-dialkylphenyl,
$R^2$ $C_1$–$C_{12}$-alkyl, phenyl, $C_1$–$C_4$-alkylphenyl, $C_2$–$C_4$-dialkylphenyl or
$R^1$+$R^2$=—$CH_2$—$CH_2$— by alkaline saponification of the corresponding $C_1$–$C_4$-alkyl esters.

Alkyl- and arylmalonic acids are important intermediates for the synthesis of agrochemicals and pharmaceutical active ingredients. They are used, for example, for the preparation of Meldrum's acids, barbiturates, fragrances and vitamins.

The preparation of substituted malonic acids is generally described in Kirk-Othmer, Encyclopedia of Chemical Technology, 3rd Edition (1981), Vol. 14, 794–810. Procedures may employ acid or alkaline saponification of esters, nitriles or amides of carboxylic acids. One problem often encountered in such processes is that the products are obtained as mixtures with sodium chloride.

Complicating factors in the preparation of the substituted malonic acids are their excellent solubility in water and their ready decarboxylation which, in the case of malonic acid, begins to occur at temperatures as low as 70° C.

The best-known preparation of methylmalonic acid starts from α-chloropropionic acid which is reacted with sodium cyanide to give the corresponding nitrile. This product is then saponified with sodium hydroxide solution, $NH_3$ being eliminated by the hydrolysis reaction. After hydrolysis, according to organic Syntheses, Vol. 11 (1943), 376, methylmalonic acid is only obtained by a laborious procedure which, at one point, requires the formation of Ca salts.

If, after the alkaline saponification of a malonic ester, the malonic acid is present as the alkali metal salt, dissolved in water, the alkali metal cations can be removed, as taught by DE-A-41 20 704, via acid ion exchangers, followed by isolation of the free acid. Since alkaline saponifications always require the use of at least stoichiometric amounts of alkali, which are neutralized again with strong acids in the course of malonic acid work-up, this process produces at least stoichiometric amounts of salt, which often have to be disposed of at considerable expense. This is a major drawback of this process of alkaline saponification.

Cyclopropane-1,1-dicarboxylic acid can be prepared in a yield of about 70%, as described in org. Syntheses, Vol. 60 (1981), 66, by the reaction of diethyl malonate 1,2-dibromoethane, sodium hydroxide solution and stoichiometric amounts of a phase transfer catalyst. Simultaneous saponification of the intermediate diethyl cyclopropane-1,1-dicarboxylate also occurs in the process. In addition to the large quantity of phase transfer catalyst required, which is 2.5 times the amount of catalyst, based on the cyclopropane-1,1-dicarboxylic acid obtained, considerable quantities of sodium chloride are also produced which, dissolved in water, require disposal.

Dimethylmalonic acid has likewise been known for a long time and can be prepared by alkaline saponification of the corresponding diethyl ester. The saponification of the dimethyl ester with potassium hydroxide solution to give the acid is mentioned by W. Schauzer, K. Clusius, Z. Physik. Chemie A 190 (1941), 243, without the yield and purity being stated. According to other processes, the acid is obtained by oxidation, employing $KMnO_4$ or $HNO_3$, of methyl precursors.

All these known processes for preparing the substituted malonic acids by alkaline saponification of the corresponding esters give rise to twice the molar amount, based on the product, of salt dissolved in water. A problem which, therefore, is inherent to all of these processes is the disposal of considerable amounts of salt solutions, which is made more difficult by official regulations. In order to reduce the degree of the disposal problem, water can be evaporated from the salt solutions. However, evaporation of water requires large amounts of energy. A need continues to exist for an improved method of isolating malonic acids simply and without requiring major use of energy.

SUMMARY OF THE INVENTION

Accordingly, one object of the present invention to provide a process by which the salts, inevitably produced in the course of alkaline hydrolysis, of malonate diester can be removed and isolated simply without major energy expenditure.

Briefly, this object and other objects of the present invention as hereinafter will become more readily apparent can be attained by process for preparing alkyl- and arylmalonic acids of the formula I:

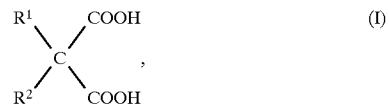

wherein
$R^1$=H, $C_1$–$C_{12}$-alkyl, phenyl, $C_1$–$C_4$-alkylphenyl, $C_2$–$C_4$-dialkylphenyl,
$R^2$=$C_1$–$C_{12}$-alkyl, phenyl, $C_1$–$C_4$-alkylphenyl, $C_2$–$C_4$-dialkylphenyl or
$R^1$+$R^2$=—$CH_2$—$CH_2$—, by alkaline saponification, comprising:
hydrolyzing the corresponding $C_1$–$C_4$-alkyl esters of the malonic acid of formula I, with alkali metal hydroxide dissolved in an aqueous alkali metal salt solution containing salt at 90–100% of saturation;
acidifying the hydrolysis product with a mineral acid;
removing the precipitated alkali metal salt which forms upon acidification; and
extracting the alkyl- and arylmalonic acid formed from the aqueous solution with the aid of an organic solvent.

DETAILED DESCRIPTION OF THE PREFERRED EMBODIMENTS

Suitable substituents $R^1$ and $R^2$ in formula I include, for example, methyl, ethyl, isopropyl, n-butyl, n-octyl, and methyl-, ethyl- or dimethylphenyl.

Examples of potentially suitable $C_1$–$C_4$-esters include the methyl, ethyl, isopropyl and n-butyl esters, preference being given to the methyl ester.

Examples of suitable alkali metal hydroxides are sodium hydroxide, potassium hydroxide, lithium hydroxide or cesium hydroxide, preference being given to sodium hydroxide or potassium hydroxide. The alkali metal hydroxide is usually employed in amounts of from 2–4 mol per mol of substituted malonic acid diester, preference being given to the use of an alkali metal hydroxide excess of from 1–50 mol %.

KOH is especially preferred, since the potassium salts are often less soluble than the sodium salts.

The alkali metal hydroxide is preferably dissolved in an aqueous saturated alkali metal salt solution. However, the concentration of salt in the salt solution normally ranges from 90% of saturation to 100% saturation.

Examples of mineral acids which can be used for this purpose include sulfuric acid, hydrochloric acid, phosphoric acid, hydriodic acid, hydrochloric acid and perchloric acid. Acidification is preferably effected with sulfuric acid or hydrochloric acid.

The aqueous solution, present after the hydrolysis, of the alkali metal salt of the substituted malonic acid is generally acidified with the mineral acid to a pH of from 1–2, the alkyl- or arylmalonic acid then being present entirely as the free acid. Based on the diester originally used, from 2–4 mols of mineral acids are most commonly used, acid preferably being employed in an excess of from 1–50 mol %.

Preference is given to an alkali metal hydroxide and an alkali metal salt solution of the same alkali metal, the acidification employing the mineral acid which corresponds to the anion of the alkali metal salt. Particular preference is given to the use of KOH as the alkali metal hydroxide, $K_2SO_4$ as the alkali metal salt and $H_2SO_4$ as the mineral acid.

The removal of the alkali metal salt which has precipitated or crystallized can be effected by filtration or centrifuging, filtration being preferred. Depending on the substituent, the alkyl- and arylmalonic acids in this situation are more or less water-soluble. The salting-out effect by itself may be sufficient to cause a fraction of the malonic acid to cocrystallize. However, crystallized malonic acid can be rapidly dissolved again if the separated solid is washed with an alcohol.

Suitable extractants generally include organic solvents which are sparingly miscible with water and sufficiently polar to take up the substituted malonic acids such as, for example, ketones, long-chain alcohols or ethers, dialkyl ethers having from 3–8 C atoms being preferred. Examples of these ether solvents include methyl ethyl ether, diethyl ether, methyl t-butyl ether, diisopropyl ether and dibutyl ether, particular preference being given to the last two mentioned.

The high salt concentrations in the aqueous phase facilitate the extraction considerably. The extraction can be effected continuously e.g. by means of a mixer-settler apparatus or batchwise by a shaking or stirring operation being carried out 2 or 3 times.

After the extraction, the solvent, optionally after it is dried, is evaporated, the alkyl- or arylmalonic acid then being produced in crystalline form. Drying can also be dispensed with, since the evaporation operation usually also goes hand in hand with azeotropic drying.

It may also be advantageous to add, towards the end of the evaporation operation, an organic nonsolvent for the alkyl- or arylmalonic acid, thereby causing the product to be precipitated and allowing it to be filtered. By means of washing and drying it is thus often possible to obtain a particularly pure product.

According to the present process, the alkali metal salts which have crystallized can be isolated by simple filtration, being produced in a sufficiently pure form to be suitable for other purposes. Having been washed with an alcohol, preferably with the alcohol formed during the hydrolysis, and having been dried, e.g. $K_2SO_4$ can be used as a fertilizer or can be employed for the preparation of alum, persulfate, potash and other products.

After the extraction of the alkyl- and arylmalonic acids the aqueous solutions can also be reused any number of times for new batches.

The process can advantageously be applied to the preparation of mono- and dialkylmalonic acids and particularly to the synthesis of phenylmalonic acid, since the equivalent of alkali, in the form of the alkali metal alcoholate, required for the synthesis of phenylmalonic acid dialkyl ester can also be utilized for the hydrolysis of the ester.

The process can also make use of the hemiesters of the alkyl- and arylmalonic acids.

Having generally described this invention, a further understanding can be obtained by reference to certain specific examples which are provided herein for purposes of illustration only and are not intended to be limiting unless otherwise specified.

EXAMPLES

Example 1

Preparation of diethylmalonic acid (DEMA)

The following are weighed into a 2 liter multinecked flask equipped with a stirrer, thermometer, dropping funnel and distilling section: 530 ml of aqueous saturated $K_2SO_4$ solution (10% strength, from previous batches), 206 g of KOH flakes (85%, 3.12 mol) and 500 ml of ethanol 95% strength (recovery from previous batches). The mixture is then heated to boiling until a clear solution is obtained. Over a period of 1 h, 270.5 g of diethyl diethylmalonate (1.25 mol) are added dropwise, and over a period of 5–6 hours from 160–180 ml of ethanol are removed by distillation. The batch is cooled. Then, with cooling (to about 25° C.), a 177 g amount of conc. $H_2SO_4$ (96% strength, 1.73 mol), which amount beforehand is diluted with about the same amount of $H_2O$, is added gradually until the pH has dropped to a level of from 1–2.

The $K_2SO_4$ which has crystallized is removed by filtration, washed twice with ethanol and is dried: 272 g (yield: 100% of the theoretical yield).

Under a partial vacuum of about 300 mbar all the ethanol is removed by distillation from the filtrate, and the DEMA is extracted from the aqueous solution by being shaken 3 times with methyl t-butyl ether (400 ml, 200 ml, 100 ml).

Methyl t-butyl ether is largely removed by distillation and replaced by toluene (400 ml). All the remaining water and methyl t-butyl ether is removed by distillation. The DEMA which has crystallized is removed by filtration, washed with toluene and dried in vacuo.

Final weight: 190 g (95% of the theoretical yield)

Purity: 99.4% (titration, GC)

Melting point: 120° C.

All the solvent distillates and the aqueous saturated $K_2SO_4$ solution (after neutralization with KOH) are reused in the subsequent batches.

Example 2

Preparation of ethylmalonic acid (EMA)

A 2 liter multinecked flask, equipped with stirrer, thermometer, dropping funnel and distillation head is charged with 600 g of aqueous saturated with $K_2SO_4$ solution-obtained from a previous batch, 203 g of KOH flakes (87%, 3.15 mol) and 350 ml of ethanol (recovered from previous batches).

The mixture is heated, with stirring, until everything has dissolved, whereupon a 282.1 g amount of diethyl ethylmalonate (1.5 mol) is added gradually over a period of 90 minutes at a temperature of 70°–80° C. During the postreaction time of from 2–3 hours, some of the alcohol (about 200 g) is removed by distillation, and the aqueous reaction solution is then, with cooling, acidified with a 168.8 g amount of $H_2SO_4$ (96% strength, 1.65 mol) which has previously been diluted with 100 ml of water. The $K_2SO_4$ which has crystallized is filtered, washed with ethanol and dried: 274 g (yield: 99.8% of the theoretical yield). All of the alcohol is distilled from the collected filtrates, in a partial vacuum of from 150–300 mbar, and the remaining aqueous solution is then extracted 4 times with methyl t-butyl ether (400 ml, 200 ml, 200 ml, 100 ml).

The organic extracts are combined and all of the methyl t-butyl ether is distilled, EMA crystallizing out in dry form.

Final weight: 191 g (96.4% of the theoretical yield)

Purity: 99.4% (titration, GC)

Melting point: 111° C.

The aqueous $K_2SO_4$-containing filtrate is neutralized with KOH and is employed for the hydrolysis in subsequent batches.

Example 3
Preparation of cyclopropane-1,1-dicarboxylic acid (CDA)

In a 4 liter multinecked flask, 800 ml of aqueous saturated $K_2SO_4$ solution (from previous batches, neutralized), 500 ml of methanol and 330 g of KOH (85%, 5.0 mol) are heated and then, at 68° C., over a period of 90 minutes, a 316.2 g amount of dimethyl cyclopropane-1,1-dicarboxylate (2.0 mol) is added gradually. During the postreaction time of 4 hours, some of the methanol distills. After the reaction solution has cooled it is acidified, with cooling, with a 281 g amount of sulfuric acid (96% strength, 2.75 mol) which has previously been diluted with 100 ml of water. The $K_2SO_4$ which crystallizes is filtered via a sintered disk, washed with methanol and dried: 380 g (87.2% of the theoretical yield).

All the methanol of the collected filtrates is removed by distillation in a partial vacuum and the aqueous solution is then extracted twice with diisopropyl ether (400 ml, 200 ml portions). The combined ether phases are briefly washed with 30 ml of water, to remove residual $K_2SO_4$, and then boiled down in vacuo until dry, the CDA precipitating in crystalline form.

Final weight: 216.9 g (83.4% of the theoretical yield)

Purity: 98.8% (titration, GC)

Melting point: 136°–137.5° C.

The distillates of the organic solvents and the aqueous $K_2SO_4$ filtrate (after neutralization with KOH) are reused in the subsequent batches.

Example 4
Preparation of phenylmalonic acid (PMA)

In a 2 liter multinecked flask equipped a distilling section, 300 g of a 32% strength potassium methylate solution (1.37 mol) are boiled down until largely dry. On top of the potassium methylate crystals, 205.5 g of ethylphenyl acetate (1.25 mol) and 826 g of diethyl carbonate (7.0 mol, fresh and recovery) are introduced, whereupon all of the methanol and ethanol is distilled at reduced pressure of about 500 mbar and a bottom temperature of about 90° C. After the end of the reaction the excess diethyl carbonate is likewise distilled in a partial vacuum until only a K salt of diethyl phenylmalonate remains.

This salt is dissolved in about 500 ml of an aqueous saturated $K_2SO_4$ solution (filtrate from previous batches), and a conc. KOH solution (130.5 g of KOH, 85%, 2.33 mol) is added. This is followed by saponification over a period of from 4–5 hours at about 90° C.

After cooling, acidification is effected carefully to a pH of about 1.5, using 201 g of conc. $H_2SO_4$ (96% strength, 1.97 mol) which have previously been diluted with $H_2O$. In the process, $K_2SO_4$ and some of the PMA is precipitated.

Work-up:

The PMA is redissolved by the addition of alcohol, $K_2SO_4$ is filtered, washed and dried, and 322 g (100% of the theoretical yield) of product is obtained. From the filtrate, after the alcohol has been removed by distillation, the PMA is obtained by extracting the filtrate 3 times with methyl t-butyl ether (800 ml). (Alternatively, PMA can be obtained directly from the salt suspension by extraction with methyl t-butyl ether, the $K_2SO_4$ crystals being filtered subsequently.)

The collected methyl t-butyl ether extracts are boiled down to dryness, and PMA crystals precipitate. The crystals are purified by being taken up in toluene, and then filtered.

Final weight: 189 g (84% of the theoretical yield)

Melting point: 152°–153° C. (decomp.)

Purity: 99.7% (titration, ion chrom.)

The preparation of PMA can equally effectively be carried out with potassium ethylate. In that case, only ethanol is produced as the distillate; the PMA crystals may assume a yellowish tinge.

The extracted phases saturated with $K_2SO_4$, and the methyl t-butyl ether distillates can be reused for subsequent batches.

Obviously, numerous modifications and variations of the present invention are possible in light of the above teachings. It is, therefore, to be understood that within the scope of the appended claims, the invention may be practiced otherwise than as specifically described herein.

What is claimed as new and is desired to be secured by letters patent of the United States is:

1. A process for preparing alkyl- and arylmalonic acids of the formula I

where $R^1$=H, $C_1$–$C_{12}$-alkyl, phenyl, $C_1$–$C_4$-alkylphenyl, $C_2$–$C_4$-dialkylphenyl, $R^2$=$C_1$–$C_{12}$-alkyl, phenyl, $C_1$–$C_4$-alkylphenyl, $C_2$–$C_4$-dialkylphenyl or $R^1$+$R^2$=—$CH_2$—$CH_2$—, by alkaline saponification, comprising:

hydrolyzing the corresponding $C_1$–$C_4$-alkyl esters of the malonic acid of formula I, with alkali metal hydroxide dissolved in an aqueous alkali metal salt solution containing salt at 90–100% of saturation;

acidifying the hydrolysis product with a mineral acid;

removing the precipitated alkali metal salt which forms upon acidification; and extracting the alkyl- and arylmalonic acid formed from the aqueous solution with the aid of an organic solvent.

2. The process as claimed in claim 1, wherein the hydrolysis is effected with sodium hydroxide or potassium hydroxide.

3. The process as claimed in claim 1, wherein the alkali metal hydroxide is dissolved in an aqueous saturated alkali metal salt solution.

4. The process as claimed in claim 1, wherein acidification is effected with hydrochloric acid or sulfuric acid.

5. The process as claimed in claim 1, wherein hydrolysis is effected with KOH in a $K_2SO_4$ solution, followed by acidification with $H_2SO_4$.

6. The process as claimed in claim 1, wherein extraction takes place with the aid of a dialkyl ether.

7. The process as claimed in claim 6, wherein extraction takes place with the aid of methyl t-butyl ether or isopropyl ether.

8. The process as claimed in claim 1, wherein the solution is acidified to a pH of from 1–2.

9. The process as claimed in claim 1, wherein, in the hydrolysis step, the amount of alkali metal hydroxide ranges from 2–4 mol per mol of malonic acid diester.

10. The process as claimed in claim 1, wherein, in the hydrolysis step, the amount of alkali metal hydroxide ranges from 1–50 mol %.

11. The process as claimed in claim 1, wherein the extracting organic solvent is a ketone, long-chain alcohol or long-chain ether.

* * * * *